United States Patent
Adam et al.

(10) Patent No.: US 6,642,247 B2
(45) Date of Patent: Nov. 4, 2003

(54) DI-OR TRIAZA-SPIRO [4,5] DECANE DERIVATIVES

(75) Inventors: Geo Adam, Schopfheim (DE); Andrea Cesura, Basel (CH); François Jenck, Riedisheim (FR); Sabine Kolczewski, Lörrach (DE); Stephan Röver, Inzlingen (DE); Jürgen Wichmann, Steinen (DE)

(73) Assignee: Hoffman-La Roche Inc., Nutley, NJ (US)

(*) Notice: Subject to any disclaimer, the term of this patent is extended or adjusted under 35 U.S.C. 154(b) by 458 days.

(21) Appl. No.: 09/330,724

(22) Filed: Jun. 11, 1999

(65) Prior Publication Data

US 2003/0176701 A1 Sep. 18, 2003

(30) Foreign Application Priority Data

Jun. 12, 1998 (EP) .............................. 98110803

(51) Int. Cl.$^7$ ................. A61K 31/438; C07D 471/10
(52) U.S. Cl. .................. 514/278; 546/16; 546/19
(58) Field of Search .................. 514/278; 546/16, 546/19

(56) References Cited

U.S. PATENT DOCUMENTS 5,221,675 A 6/1993 Chung et al.

FOREIGN PATENT DOCUMENTS

| EP | 0 856 514 | 8/1998 | |
|---|---|---|---|
| JP | 63-208844 | * 8/1988 | ............ 549/19 |
| WO | WO 95/03303 | 2/1995 | |

OTHER PUBLICATIONS

Database Chem. Abstract XP–002153586=JP 63 208844 A.
U.S. patent application Ser. No. 09/009,457, Adam et al., (pending).
U.S. patent application Ser. No. 09/204,184, Adam et al., (pending).
U.S. patent application Ser. No. 09/330,851, Adam et al., (pending).
Julius, *Nature* 377:476 (1995).
Meunier, *Eur. J. Pharmacol.*, 340:1–15 (1997).
Henderson et al., *Trends Pharmacol. Sci.*, 18:293–300 (1997).
Mogil, et al., *Neuroscience*, 75:333–337 (1996).
Vanderah et al., *Eur. J. Pain*, 2:267–280 (1998).
Jenck et al., *Proc. Natl. Acad. Sci., USA*, 94:14854–14858 (1997).
Pomonis et al., *Neuroreport*, 8:369–371 (1996).
Manabe et al., *Nature*, 394:577–581 (1998).
Peluso et al., *J. Neuroimmmuno*, 81:184–192 (1998).
Porro et al., *Prog. Clin. Biol. Res.* 397:315–325 (1998).
Ito et al., *Heterocycles* 36:21–24 (1993).
Bunzow et al., *Febs Lett.* 347:284–288 (1994).
Cheng et al., *Biochem. Pharmacol.*, 22:309–3108 (1973).
Doepp et al., *Chem. Ber.* 121:1651–1655 (1998).
Isuge et al., *Chem. Lett.* pp. 923–976 (1986).

* cited by examiner

Primary Examiner—C. S. Aulakh
(74) Attorney, Agent, or Firm—George W. Johnston; Patricia S. Rocha-Tramaloni; Kimberly J. Prior

(57) ABSTRACT

The present invention relates to compounds of the general formula

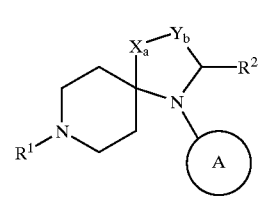

I wherein $R^1$ is $C_{6-10}$-cycloalkyl, optionally substituted by lower alkyl or —C(O)O-lower alkyl; decahydro-naphthalen-1-yl; decahydro-naphthalen-2-yl; indan-1-yl or indan-2-yl, optionally substituted by lower alkyl; decahydro-azulen-2-yl; bicyclo[6.2.0]dec-9-yl; acenaphthen-1-yl; 2,3-dihydro-1H-phenalen-1-yl; 2,3,3a,4,5,6-hexahydro-1H-phenalen-1-yl or octahydro-inden-2-yl;

$R^2$ is hydrogen; lower alkyl; =O or phenyl, optionally substituted by lower alkyl, halogen or alkoxy;

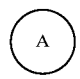

is cyclohexyl or phenyl, optionally substituted by lower alkyl, halogen or alkoxy;

X is —CH(OH)—; —C(O)—; —CHR$^3$—; —CR$^3$=; —O—; —S—; —CH(COOR$^4$)— or C(COOR$^4$)=;

Y is —CH$_2$—; —CH=; —CH(COOR$^4$)—, —C(COOR$^4$)=; or —C(CN)—;

$R^3$ is hydrogen or lower alkoxy;

$R^4$ is lower alkyl, cycloalkyl, phenyl, or benzyl and either a or b is optionally an additional bond, and to pharmaceutically acceptable acid addition salts thereof.

The compounds are agonists of the orphanin FQ (QFQ) receptor and therefore useful in the treatment of diseases, related to this receptor.

20 Claims, No Drawings

DI- OR TRIAZA-SPIRO [4,5] DECANE DERIVATIVES

FOREIGN PRIORITY CLAIMED

This application is based on EP Patent Application No. 98110803.8 filed on Jun. 12, 1998 and claims priority thereto under 35 U.S.C. §119(a)–(d) or 35 U.S.C. §365(a)–(b).

FIELD OF THE INVENTION

This invention relates to di- or triaza-spiro [4,5] decane derivatives particularly wherein $R^1$ is $C_{6-10}$cycloalkyl which may be substituted or unsubstituted or wherein $R^1$ is decahydro-naphthalen-2-yl and compositions thereof.

BACKGROUND OF THE INVENTION

OFQ, a heptadeca peptide, has been isolated from rat brain and is a natural ligand to a G-protein coupled receptor (OFQ-R), found at high levels in brain tissue. OFQ exhibits agonistic activity at the OFQ-R both in vitro and in vivo.

Julius (Nature 377, 476, [1995]) discusses the discovery of OFQ noting that this peptide shares greatest sequence homology with dynorphin A, an established endogenous ligand for opioid receptors. OFQ inhibits adenylate cyclase in CHO(LC 132⁺) cells in culture and induces hyperalgesia when administered intra-cerebroventricularly to mice. The pattern of results indicate that this heptadecapeptide is an endogenous agonist of the LC 132 receptor and it appears to have pro-nociceptive properties. It has been described that when injected intra-cerebroventricularly in mice, OFQ slowes down locomotive activity and induces hyperalgesia and it has been concluded that OFQ may act as a brain neurotransmitter to modulate nociceptive and locomotive behavior.

It has been found that the compounds of the present invention interact with the orphanin FQ (OFQ) receptor and consequently are useful in the treatment of a variety of psychiatric, neurological and physiological disorders.

In the following references some of these indications have been described:

Nociceptin/orphanin FQ and the opioid receptor-like ORL1 receptor, *Eur. J. Pharmacol.,* 340: 1–15, 1997;

The orphan opioid receptor and its endofenous ligand ociceptin/orphanin FQ, *Trends Pharmacol. Sci.,* 18:293–300, 1997;

Orphanin FQ is a functional anti-opioid peptide, *Neuroscience,* 75:333–337, 1996;

Orphanin FQ/nociceptin-lack of antinociceptive, hyperalgesic or allodynic effects in acute thermal or mechanical tests, following intracerebroventricular or intrathecal administration to mice or rats, *Eur. J. pain,* 2: 267–280, 1998;

Orphanin FQ acts as an anxiolytic to attenuate behavioral responses to stress, *Proc. Natl. Acad. Sci., USA,* 94: 14854–14858, 1997;

Orphanin FQ, an agonist of orphan opioid receptor ORL1, stimulates feeding in rats, *Neuroreport,* 8: 369–371, 1996;

Facilitation of long-term potentiation and memory in mice lacking nociceptin receptors, *Nature,* 394: 577–581, 1998;

Distribution of nociceptin/orphanin FQ receptor transcript in human central nervous system and immune cells, *J. Neuroimmuno,* 81: 184–192, 1998;

Orphanin FQ plays a role in sepsis, *Prog. Clin. Biol. Res.* (1998), 397, 315–325.

Objects of the present invention are the compounds of formula I and pharmaceutically acceptable addition salts thereof, racemic mixtures and their corresponding enantiomers, the preparation of the above-mentioned compounds, medicaments containing them and their manufacture as well as the use of the above-mentioned compounds in the control or prevention of illnesses, especially of illnesses and disorders of the kind referred above, or in the manufacture of corresponding medicaments.

SUMMARY OF THE INVENTION

The present invention relates to compounds of the general formula

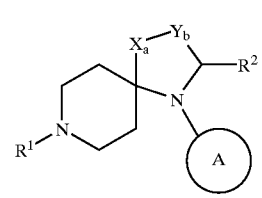

wherein
$R^1$ is $C_{6-10}$-cycloalkyl, optionally substituted by lower alkyl or —C(O)O-lower alkyl; decahydro-naphthalen-1-yl; decahydro-naphthalen-2-yl; indan-1-yl or indan-2-yl, optionally substituted by lower alkyl; decahydro-azulen-2-yl; bicyclo[6.2.0]dec-9-yl; acenaphthen-1-yl; 2,3-dihydro-1H-phenalen-1-yl; 2,3,3a,4,5,6-hexahydro-1H-phenalen-1-yl or octahydro-inden-2-yl;
$R^2$ is hydrogen; lower alkyl; =O or phenyl, optionally substituted by lower alkyl, halogen or alkoxy;

(A)

is cyclohexyl or phenyl, optionally substituted by lower alkyl, halogen or alkoxy;
X is —CH(OH)—; —C(O)—; —CHR³—; —CR³=; —O—; —S—; —CH(COOR⁴)— or —C(COOR⁴)=;
Y is —CH₂—; —CH=; —CH(COOR⁴)—, —C(COOR⁴)=; or —C(CN)—;
$R^3$ is hydrogen or lower alkoxy;
$R^4$ is lower alkyl, cycloalkyl, phenyl, or benzyl;
and
either a or b is optionally an additional bond,
and to pharmaceutically acceptable acid addition salts thereof.

The compounds of formula I and their salts are characterized by valuable therapeutic properties. It has surprisingly been found that the compounds of the present invention are agonists of the orphanin FQ (OFQ) receptor. Consequently they are useful in the treatment of psychiatric, neurological and physiological disorders, especially, but not limited to, amelioration of symptoms of anxiety and stress disorders, depression, trauma, memory loss due to Alzheimer's disease or other dementias, epilepsy and convulsions, acute and/or chronic pain conditions, symptoms of addictive drug withdrawal, control of water balance, Na⁺ excretion, arterial blood pressure disorders and metabolic disorders such as obesity.

DETAILED DESCRIPTION OF THE INVENTION

The following definitions of the general terms used in the present description apply irrespective of whether the terms in question appear alone or in combination, such as lower alkyl and lower alkoxy.

The term "lower alkyl" denotes a straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" denotes a saturated carbocyclic group containing from 5–15 carbon atoms, preferred are cyclohexyl, cyclooctyl, cyclononyl and cyclodecyl.

The term "halogen" denotes chlorine, iodine, fluorine and bromine.

The term "pharmaceutically acceptable acid addition salts" embraces salts with inorganic and organic acids well-known in the art for pharmaceutic purposes, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present invention are those of formula I, in which $R^1$ is $C_{6-10}$-cycloalkyl, optionally substituted by lower alkyl, $R^2$ is hydrogen, X is —CH(OH)—, —C(O)— or —CHOCH$_3$ and Y is —CH$_2$—, for example the following compounds:

(RS)-8-(cis-4-Isopropyl-cyclohexyl)-1-phenyl-1,8-diaza-spiro[4.5]decan-4-ol,
(R)-8-(cis-4-Isopropyl-cyclohexyl)-1-phenyl-1,8-diaza-spiro[4.5]decan-4-ol,
(S)-8-(cis-4-Isopropyl-cyclohexyl)-1-phenyl-1,8-diaza-spiro[4.5]decan-4-ol,
8-(cis-4-Isopropyl-cyclohexyl)-1-phenyl-1,8-diaza-spiro[4.5]decan-4-one,
(RS)-8-(cis-4-Isopropyl-cyclohexyl)-4methoxy-1-phenyl-1,8-diaza-spiro[4.5]decane,
and
(RS)-8-Cyclononyl-1-phenyl-1,8-diaza-spiro[4.5]decan-4-ol.

Further preferred are compounds of formula I, in which $R^1$ is decahydro-naphthalen-2-yl, 2,3,3a,4,5,6-hexahydro-1H-phenalen-1-yl, 4-methyl-indan-2-yl, octahydro-inden-2-yl and decahydro-azulen-2-yl, $R^2$ is hydrogen, X is —CH(OH)— or —CHOCH$_3$ and Y is —CH$_2$—.

Examples of such compounds are
(RS)- and (SR)-8-[(2RS,4aSR,8aRS)-decahydro-naphthalen-2-yl]-1-phenyl-1,8-diaza-spiro[4.5]decan-4-ol,
8-(decahydro-naphthalen-2-yl)-1-phenyl-1,8-diaza-spiro[4.5]decan-4-ol,
8-(2,3,3a,4,5,6-hexahydro-1H-phenalen-1-yl)-1-phenyl-1,8-diaza-spiro[4.5]decan-4-ol,
(RS)- and (SR)-8-[(RS)-(4-methyl-indan-2-yl)]-1-phenyl-1,8-diaza-spiro[4.5]decan-4-ol,
8-(decahydro-azulen-2-yl)-1-phenyl-1,8-diaza-spiro[4.5]decan-4-ol or
8-(octahydro-inden-2-yl)-4-methoxy-1-phenyl-1,8-diaza-spiro[4.5]decane (mixture of diastereoisomers).

The present compounds of formula I and their pharmaceutically acceptable salts can be prepared by methods known in the art, for example, by the processes described below, which comprise a) reductively aminating a compound of formula

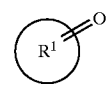

II with a compound of formula

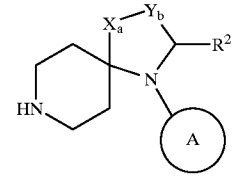

III wherein $R^1$, $R^2$, a, b,

,

X and Y have the significances given above, or b) reducing a compound of formula

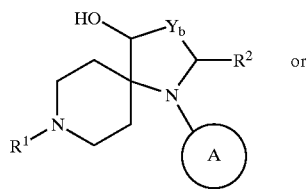

I-1 or

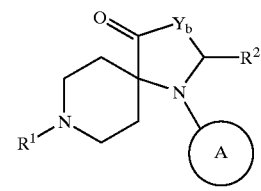

I-3 to a compound of formula

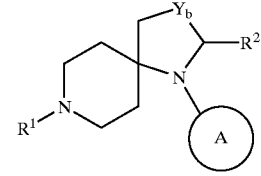

I-2 wherein $R^1$, $R^2$, b,

and Y have the significances given above, or c) oxidizing a compound of formula

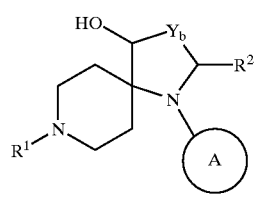

I-1 to a compound of formula

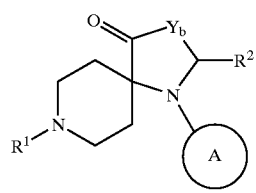

I-3 wherein $R^1$, $R^2$, b,

and Y have the significances given above, or
d) reducing a compound of formula I-3 to a compound of formula

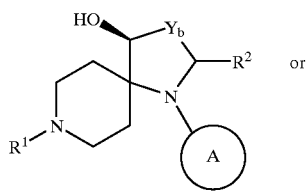

I-1-1 or

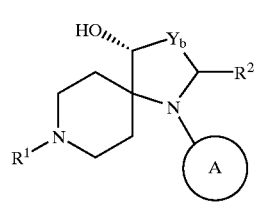

I-1-2 wherein $R^1$, $R^2$, b,

and Y have the significances above, or
e) alkylating a compound of formula I-1 to a compound of formula I, wherein X is —CH(lower alkoxy)-, or
f) hydrogenating a compound of formula I, wherein

is phenyl, to a compound of formula I, wherein

is cyclohexyl, or
g) treating a compound of formula

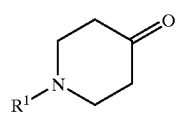

IV with an amino thiol of the formula

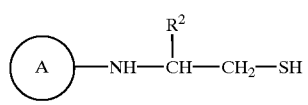

V to give a compound of formula

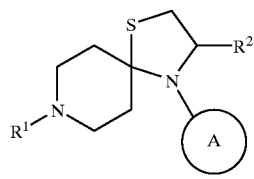

I-4 wherein $R^1$ and

have the significances given above and $R^2$ is hydrogen or phenyl, or h) treating a compound of formula

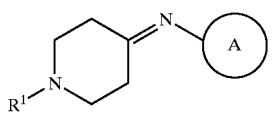

VII with a compound of formula

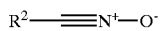

IX to give a compound of formula

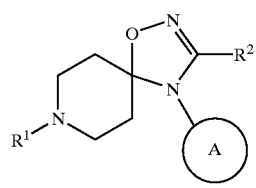

wherein $R^1$ and

have the significances given above, and $R^2$ is phenyl, optionally substituted by lower alkyl, halogen or alkoxy, and if desired converting a racemic mixture into its enantiomeric components thus obtaining optically pure compounds, and converting a compound of formula I obtained into a pharmaceutically acceptable acid addition salt.

In accordance with process variant a) the reductive amination of a keto compound of formula II with an amine of formula III is carried out by stirring with a dehydrating agent in the presence of molecular sieves (4Å), in an inert solvent, such as toluene or tetrahydrofuran (THF), at reflux temperature. An alternative method is the dehydration in the presence of an acidic catalyst with removal of water, e.g. with azeotropic removal of water, or with tetraisopropyl-orthotitanate in THF.

The obtained intermediate enamine or imine is then reduced with a reducing agent, such as metal hydrides or hydrogen in the presence of a hydrogenating catalyst, preferably with sodium cyanoborohydride in a protic solvent, for example in a mixture of THF and ethanol at acidic pH.

Examples for corresponding keto compounds of formula II are the following:

cis-octahydro-2(1H)-naphthalenone, 4-(1-methylethyl)-cyclohexanone, 2-indanone, 4-ethyl-cyclohexanone, 1,3-dihydro-4-methyl-2H-inden-2-one, 4-oxo-cyclohexanecarboxilic acid ethyl ester, cyclodecanone, (3a,RS,8aRS)-decahydro-azulen-2-on, cis-octahydro-inden-2-one, cyclooctanone or cis-bicyclo[6.2.0]dec-9-one.

In accordance with process variant b) a compound of formula I-1 or I-3 is reduced to a compound of formula I-2. This process is carried out in conventional manner with a reducing agent, preferably a metal hydride, such as lithium aluminium hydride in an aprotic solvent, for example in diethylether.

In accordance with process variant c) a compound of formula I-1 is oxidized in an inert solvent, such as in acetic anhydride in DMSO at room temperature or with 4-methyl-morpholine-4-oxide in the presence of tetra-n-propylammonium-perruthenate and molecular sieves in dichloromethane at room temperature.

The reduction of a compound of formula I-3 to a compound of formula I-1-1 and/or to I-1-2 is carried out with an inert solvent, for example in the presence of an enantioselective (enantiopure) reagent or catalyst to achieve an enantiospecific formation of one enantiomer. Preferred enantioselective reagents are chiral oxazaborolidines. The reaction is carried out in the presence of borane-dimethylsulfide in THF at about room temperature. The chiral oxazaborolidines are formed in situ from chiral 1-amino-2-indanols and borane-dimethylsulfide.

In accordance with process variant e) a compound of formula I-1 is alkylated. The preferred alkylating agent is dimethylsulfate. The process is carried out in conventional manner in an inert solvent with sodium hydride in dimethylformamide.

In process variant f) is described the hydrogenation of a compound of formula I, wherein

is phenyl. The desired cyclohexyl ring is yielded in a protic solvent, such as methanol and in the presence of a hydrogenating catalyst, for example in the presence of platinum oxide. The reaction is carried out under hydrogen pressure between 1 and 50 bar.

The formation of a 1,3-thiazolidine derivative is described in process variant g). The reaction is carried out by treating a mixture of a ketone and an amino thiol with a Lewis acid, such as boron trifluoride diethyl ether complex, in a chlorinated solvent, for example in dichloromethane.

The process step h) describes the cycloaddition of an imine of formula VII with a nitrile oxide of formula IX to give a compound of formula I-6. The process is carried out by treating an imine with a slight excess of a corresponding hydroximinoyl chloride and a base, such as triethylamine, in an inert solvent, for example in THF, described in general in Heterocycles 36, 21–24, 1993.

Racemic mixtures can be converted into its enantiomeric components in conventional manner, for example by preparative HPLC.

The salt formation is effected at room temperatures in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methanesulphonates, p-toluenesulfonates and the like are examples of such salts.

The compounds of formula II, III, IV, V, VII, VIII, IX and XII which are used as starting materials are known compounds or can be prepared by methods known per se.

The following scheme 1 describes the cyclization of compounds of formulae IX and XII to yield compounds of formulae I-7 and I-1-3. Scheme 2 describes possible reaction variants to yield compounds of formulae I-5 and I-6 and scheme 3 describes the preparation of compounds of formula I, wherein X is S.

Scheme 1

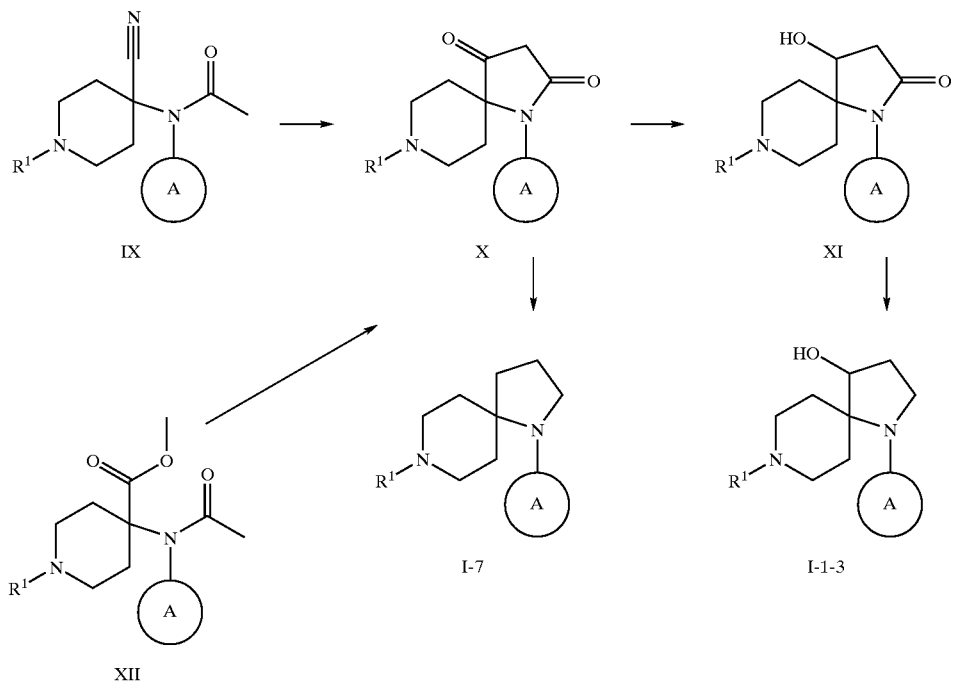

wherein $R^1$ and

have the significances given above.

Scheme 2

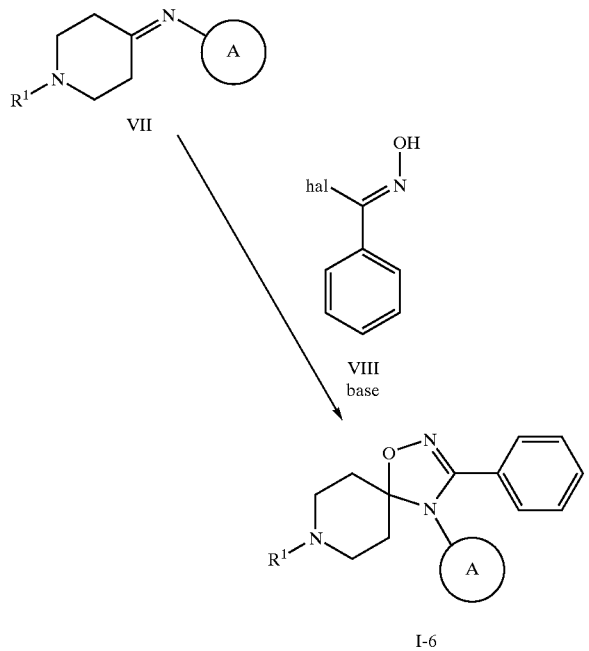

wherein $R^1$ and

have the significances given above.

Scheme 3

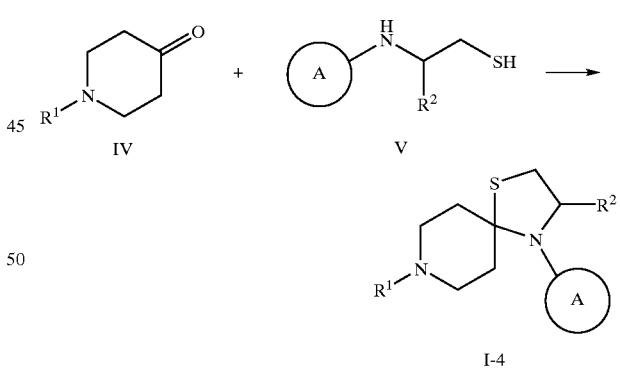

wherein $R^1$, $R^2$ and

have the significances given above.

As mentioned earlier, the compounds of formula I and their pharmaceutically usuable addition salts possess valuable pharmacodynamic properties. It has been found that the compounds of the present invention are agonists of the OFQ receptor and have effects in animal models of psychiatric, neurological and physiological disorders, such as anxiety, stress disorders, depression, trauma, memory loss due to Alzheimer's disease or other dementias, epilepsy and convulsions, acute and/or chronic pain conditions, symptoms of addictive drug withdrawal, control of water balance, $Na^+$ excretion, arterial blood pressure disorders and metabolic disorders such as obesity.

The compounds were tested for pharmacologic activity in accordance with the methods given hereinafter:

Methods of OFQ-R Binding Assay

Cell Culture

HEK-293 cells adapted to suspension growth (293s) were cultured in HL medium plus 2% FBS. The cells were transfected with the rat OFQ receptor cDNA (LC132), FEBS Lett. 347, 284–288, 1994, cloned in the expression vector pCEP4 (Invitrogen, San Diego, Calif., USA) using lipofectin (Life Technologies, Bethesda, Md., USA). Transfected cells were selected in the presence of hygromycin (1000 U/ml) (Calbiochem, San Diego, Calif., USA). A pool of resistant cells was tested for OFQ-R expression by binding of $[^3H]$-OFQ (Amersham PLC, Buckinghamshire, England). These cells (293s-OFQ-R) were expanded for large scale culture and membrane preparation.

Membrane preparation

293s-OFQ-R cells were harvested by centrifugation, washed 3 times with phosphate buffered saline (PBS) before resuspension in buffer A (50 mM Tris-HCl, pH 7.8, 5 mM $MgCl_2$, 1 mM EGTA) and disruption with a tissue homogenizer (30 seconds, setting 4, Pt 20, Kinematica, Kriens-Lucern, Switzerland). A total membrane fraction was obtained by centrifugation at 49,000×g at 4° C. This procedure was repeated twice and the pellet was resuspended in buffer A. Aliquots were stored at −70° C. and protein concentrations were determined using the BCA™ Protein Assay Reagent (Pierce, Rockford, Ill.) following the manufacturer's recommendations.

Binding Assays $[^3H]$-OFQ competition studies were carried out with 77 μg membrane protein in a final assay volume of 0.5 ml buffer A plus 0.1% BSA and 0.01% bacitracin (Boehringer-Mannheim, Mannheim, Germany) for one hour at room temperature. 50 nM unlabeled OFQ was used to define the non-specific binding. The assays were terminated by filtration through Whatman GF/C filters (Unifilter-96, Canberra Packard S.A., Zurich, Switzerland) pretreated with 0.3% polyethylenimine (Sigma, St. Louis, Mo., USA) and 0.1% BSA (Sigma) for 1 hour. The filters were washed 6 times with 1 ml of ice bold 50 mM Tris-HCl pH 7.5. The retained radioactivity was counted on a Packard Top-Count microplate scintillation counter after addition of 40 μl of Microscint 40 (Canberra Packard). The effects of compounds were determined using at least 6 concentrations in triplicate, and determined twice. $IC_{50}$ values were determined by curve fitting and these calues were converted to $K_i$ values by the method of Cheng and Prusoff, Biochem. Pharmacol., 22, 3099, 1973.

The affinity to the OFQ-receptor, given as $pK_i$, is in the range of 7.1 to 9.8. For example, the $pK_i$-values of 8-(cis-4-Isopropyl-cyclohexyl)-1-phenyl-1,8-diaza-spiro[4.5]decan-4-one (Ex1.6) and (RS)-8-Acenaphthalen-1-yl-1-phenyl-1,8-diaza-spiro[4.5]decane (Ex1.19) are 9.4 and 8.6, respectively.

GTPγS Binding Assay

This assay was used to define whether the compounds of this invention are agonists or antagonists of the OFQ receptor.

Agonist-mediated binding of GTPγS was investigated in 96-well plates using a Scintillation Proximity Assay (SPA) using either hOFQR membranes or membranes prepared from cells transfected with the various human opiate receptors (μ, δ and κ). Binding was performed in 200 μl 20 mM HEPES-buffer (pH 7.4, plus 6 mM $MgCl_2$ and 100 mM NaCl), supplemented with 20 μM GDP, 10 μm cold GTPγS and 0.3 nM $GTP[\gamma^{35}]S$ (1130 Ci/mmol). Twenty μg membranes, 1 mg wheatgerm agglutinin SPA beads (Amersham, Little Chalfont, UK) and either OFQ ($10^{-5}$ to $10^{-10}$ M) or synthetic compounds ($10^{-4}$ M to $10^{-9}$ M) were added.

The reaction mixture was incubated on a shaker for 60 min at 22° C. and then centrifuged for 5 min at 1500 rpm in an Eppendorf 5403 centrifuge. Finally the plates were read in a Top counter (Packard).

Compounds of this invention have been shown to be agonists of the OFQ receptor having $PEC_{50}$ ranges from about 5.6 to about 7.2.

The preparation of the following compounds is described in Examples 1–53:

I

| A | R¹ | R² | X | Y | Optional Bond a/b | Ex. |
|---|---|---|---|---|---|---|
| phenyl | 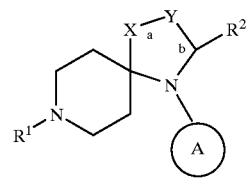 | H₂ | CHOH | CH₂ | no | 1 |

-continued

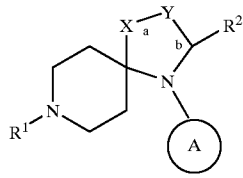

I

| A | R¹ | R² | X | Y | Optional Bond a/b | Ex. |
|---|----|----|---|---|-------------------|-----|
| phenyl | 4-isopropylcyclohexyl | H₂ | CHOH | CH₂ | no | 2 |
| phenyl | 2-indanyl | H₂ | CHOH | CH₂ | no | 3 |
| phenyl | trans-4-isopropylcyclohexyl | H₂ | CHOH | CH₂ | no | 4 |
| phenyl | 2-indanyl | H₂ | CO | CH₂ | no | 5 |
| phenyl | 4-isopropylcyclohexyl | H₂ | CO | CH₂ | no | 6 |
| phenyl | 4-ethylcyclohexyl | H₂ | CHOH | CH₂ | no | 7 |
| phenyl | 4-methyl-2-indanyl | H₂ | CHOH | CH₂ | no | 8 |
| phenyl | 4-(ethoxycarbonyl)cyclohexyl | H₂ | CHOH | CH₂ | no | 9 |
| phenyl | cyclooctyl | H₂ | CHOH | CH₂ | no | 10 |

-continued
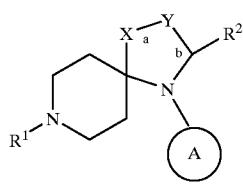
I
| A | R¹ | R² | X | Y | Optional Bond a/b | Ex. |
|---|---|---|---|---|---|---|
| phenyl | cyclodecyl | H₂ | CHOH | CH₂ | no | 11 |
| phenyl | bicyclic (7+5) | H₂ | CHOH | CH₂ | no | 12 |
| phenyl | bicyclic (6+5) with H | H₂ | CHOH | CH₂ | no | 13 |
| phenyl | cyclooctyl | H₂ | CHOH | CH₂ | no | 14 |
| phenyl | bicyclic (8+4) with H | H₂ | CHOH | CH₂ | no | 15 |
| phenyl | acenaphthyl | H₂ | CHOH | CH₂ | no | 16 |
| phenyl | phenalenyl | H₂ | CHOH | CH₂ | no | 17 |

-continued
I
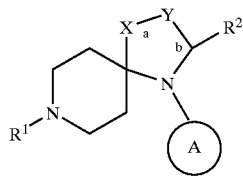
| A | R¹ | R² | X | Y | Optional Bond a/b | Ex. |
|---|---|---|---|---|---|---|
| phenyl | | H₂ | CHOH | CH₂ | no | 18 |
| phenyl | | H₂ | CH₂ | CH₂ | no | 19 |
| phenyl | | H₂ | CO | CH₂ | no | 20 |
| phenyl | | =O | CHOH | CH₂ | no | 21 |
| phenyl | | H₂ | CO | CH₂ | no | 22 |
| phenyl | | H₂ | CO | CH₂ | no | 23 |
| phenyl | | H₂ | CO | CH₂ | no | 24 |

-continued

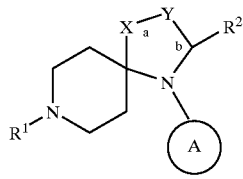

I

| A | R¹ | R² | X | Y | Optional Bond a/b | Ex. |
|---|---|---|---|---|---|---|
| phenyl | *trans-bicyclic (octahydroindene), H/H* | H₂ | CO | CH₂ | no | 25 |
| phenyl | *tricyclic (phenalene-derived), H* | H₂ | CO | CH₂ | no | 26 |
| phenyl | *cyclodecyl* | H₂ | CO | CH₂ | no | 27 |
| phenyl | *cyclononyl* | H₂ | CO | CH₂ | no | 28 |
| phenyl | *trans-bicyclic (octahydroindene), H/H* | H₂ | CH₂ | CH₂ | no | 29 |
| phenyl | *cyclodecyl* | H₂ | CH₂ | CH₂ | no | 30 |
| phenyl | *4-isopropylcyclohexyl* | H₂ | $-\overset{OCH_3}{\underset{H}{C}}-$ | CH₂ | no | 31 |
| phenyl | *4-isopropylcyclohexyl* | H₂ | CO | CH₂ | no | 32 |
| phenyl | *4-isopropylcyclohexyl* | H₂ | $-\overset{OH}{CH}-$ | CH₂ | no | 33 |

-continued

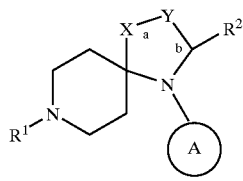

I

| A | R¹ | R² | X | Y | Optional Bond a/b | Ex. |
|---|---|---|---|---|---|---|
| phenyl | isopropylcyclohexyl | H₂ | —CH(OH)— | CH₂ | no | 34 |
| phenyl | 4-methylindanyl | H₂ | CO | CH₂ | no | 35 |
| phenyl | octahydroindanyl (trans H,H) | H₂ | —CH(OCH₃)— | CH₂ | no | 36 |
| cyclohexyl | octahydroindanyl (trans H,H) | H₂ | CHOH | CH₂ | no | 37 |
| phenyl | isopropylcyclohexyl | H₂ | S | CH₂ | no | 38 |
| phenyl | isopropylcyclohexyl | H | —C(COOCH₃) | —C(COOCH₃) | a | 39 |
| phenyl | decahydronaphthyl (trans H,H) | O | —CH(OH)— | CH₂ | no | 40 |
| phenyl | decahydronaphthyl (trans H,H) | H₂ | —CH(OH)— | CH₂ | no | 41 |
| phenyl | decahydronaphthyl (trans H,H) | H₂ | —CO— | CH₂ | no | 42 |

-continued
I
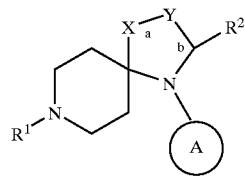
| A | R¹ | R² | X | Y | Optional Bond a/b | Ex. |
|---|----|----|---|---|---|-----|
| phenyl | tricyclic (perhydrophenalene, H) | H₂ | —C(OH)(H)— | CH₂ | no | 43 |
| phenyl | tricyclic (perhydrophenalene, H) | H₂ | —C(OCH₃)(H)— | CH₂ | no | 44 |
| phenyl | acenaphthenyl | H₂ | —C(OCH₃)(H)— | CH₂ | no | 45 |
| phenyl | cyclodecyl | H₂ | —C(OCH₃)(H)— | CH₂ | no | 46 |
| phenyl | cyclooctyl | H₂ | —C(OCH₃)(H)— | CH₂ | no | 47 |
| phenyl | bicyclo[6.2.0] (H,H) | H₂ | —C(OCH₃)(H)— | CH₂ | no | 48 |
| phenyl | cycloundecyl | H₂ | —C(OCH₃)(H)— | CH₂ | no | 49 |

-continued

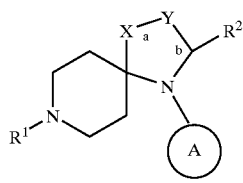

I

| A | R¹ | R² | X | Y | Optional Bond a/b | Ex. |
|---|---|---|---|---|---|---|
| phenyl | (bicyclic: cycloheptane fused with cyclopentane) | H₂ | —C(OCH₃)H— | CH₂ | no | 50 |
| phenyl | 4-isopropylcyclohexyl | H₂ | —CH(COOCH₃)— | —CH(COOCH₃)— | no | 51 |
| phenyl | 4-isopropylcyclohexyl | H₂ | —CH(COOCH₃)— | =CH(COOCH₃)— | no | 52 |
| phenyl | 4-isopropylcyclohexyl | — | —O— | —N= | b | 53 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, the effective dosage for oral or parenteral administration is 0.01–20 mg/kg/day, preferred as a dosage of 0.1–10 mg/kg/day for all described indications. The dayly dosage for an adult of 70 kg weight is therefore between 0.7–1400 mg/day, preferred is 7–700 mg/day, although the above upper limit can also be exceeded when necessary.

The following Examples illustrate the present invention without limiting it. All temperatures are given in degrees Celsius.

EXAMPLE 1

8-(Decahydro-naphthalen-2-yl)-1-phenyl-1,8-diaza-spiro[4.5]decan-4-ol hydrochloride (1:1)

Mixture of Isomers, Configuration at (4a,8a) is cis cis-Octahydro-2(1H)-naphthalenone (1.1 mmol) was dissolved in toluene, (RS)-1-phenyl-1,8-diaza-spiro[4.5]decan-4-ol (1.1 mmol) and molecular sieves (4Å, 1.0 g) were added. The mixture was refluxed with stirring for 16 h, filtered and the filtrate was evaporated. The residue was dissolved in THF/ethanol (10 ml, 9:1), sodium cyanoborohydride (1.1 mmol) was added and the pH was adjusted to 4. The mixture was stirred for 3 h at room temperature. Ice-water (30 ml) and potassium carbonate solution (50%, 10 ml) were added. The mixture was extracted twice with dichloromethane, organic phases were pooled, dried with MgSO4 and concentrated. Chromatography on silica gel (methylenchloride/methanol, 98:2) yielded the desired product which was crystallized as its HCl-salt from ethanol. 65 mg (16%) 8-(decahydro-naphthalen-2-yl)-1-phenyl-1,8-diaza-spiro[4.5]decan-4-ol hydrochloride (1:1) as a colorless solid, m.p.>250° C. and MS: m/e=369.3 (M+H$^+$).

EXAMPLE 2

(RS)-8-(cis-4-Isopropyl-cyclohexyl)-1-phenyl-1,8-diaza-spiro[4.5]decan-4-ol hydrochloride (1:1)

The title compound, m.p.>250° C. and MS: m/e=357.3 (M+H$^+$) was prepared in accordance with the general method of example 1 from 4-(1-methylethyl)-cyclohexanone and (RS)-1-phenyl-1,8-diaza-spiro[4.5]decan-4-ol.

EXAMPLE 3

(RS)-8-Indan-2-yl-1-phenyl-1,8-diaza-spiro[4.5]decan-4-ol hydrochloride (1:1)

The title compound, m.p.>250° C. and MS: m/e=349.4 (M+H$^+$) was prepared in accordance with the general method of example 1 from 2-indanone and (RS)-1-phenyl-1,8-diaza-spiro[4.5]decan-4-ol.

EXAMPLE 4

(RS)-8-(trans-4-Isopropyl-cyclohexyl)-1-phenyl-1,8-diaza-spiro[4.5]decan-4-ol hydrochloride (1:1)

The title compound, m.p.>250° C. and MS: m/e=357.3 (M+H$^+$) was prepared in accordance with the general method of example 1 from 4-(1-methylethyl)-cyclohexanone and (RS)-1-phenyl-1,8-diaza-spiro[4.5]decan-4-ol.

EXAMPLE 5

8-Indan-2-yl-1-phenyl-1,8-diaza-spiro[4.5]decan-4-one hydrochloride (1:1)

(RS)-8-Indan-2-yl-1-phenyl-1,8-diaza-spiro[4.5]decan-4-ol (2.0 mmol) was dissolved in DMSO (12 ml), acetic anhydride (0.6 ml) was added and the mixture was stirred for 24 h at room temperature. The solvents were removed in vacuo. Chromatography on silica gel (methylenchloride/methanol, 98:2) yielded the desired product which was crystallized as its HCl-salt from ethyl acetate. 0.37 g (48%) 8-indan-2-yl-1-phenyl-1,8-diaza-spiro[4.5]decan-4-one hydrochloride (1:1) as a colorless solid, m.p.>250° C. and MS: m/e=347.4 (M+H$^+$).

EXAMPLE 6

8-(cis-4-Isopropyl-cyclohexyl)-1-phenyl-1,8-diaza-spiro[4.5]decan-4-one hydrochloride (1:1)

The title compound, m.p.226–228° C. and MS: m/e=355.4 (M+H$^+$) was prepared in accordance with the general method of example 5 from (RS)-8-(cis-4-isopropyl-cyclohexyl)-1-phenyl-1,8-diaza-spiro[4.5]decan-4-ol.

EXAMPLE 7

Mixture of (RS)-8-cis and trans-4-ethyl-cyclohexyl)-1-phenyl-1,8-diaza-spiro[4.5]decan-4-ol hydrochloride (1:1)

The title compound, m.p.>250° C. and MS: m/e=343.4 (M+H$^+$) was prepared in accordance with the general method of example 1 from 4-ethyl-cyclohexanone and (RS)-1-phenyl-1,8-diaza-spiro[4.5]decan-4-ol.

EXAMPLE 8

Mixture of (RS)- and (SR)-8[(RS)-(4-Methyl-indan-2-yl)]-1-phenyl-1,8-diaza-spiro[4.5]decan-4-ol hydrochloride (1:1)

The title compound, m.p.>250° C. and MS: m/e=363.2 (M+H$^+$) was prepared in accordance with the general method of example 1 from 1,3-dihydro-4-methyl-2H-inden-2-one and (RS)-1-phenyl-1,8-diaza-spiro[4.5]decan-4-ol.

EXAMPLE 9

(RS)-4-cis-(4-Hydroxy-1-phenyl-1,8-diaza-spiro[4.5]dec-8-yl)-cyclohexanecarboxylic acid ethyl ester hydrochloride (1:1)

The title compound, m.p.>225° C. dec. and MS: m/e=387.3 (M+H$^+$) was prepared in accordance with the general method of example 1 from 4-oxo-cyclohexanecarboxylic acid ethyl ester and (RS)-1-phenyl-1,8-diaza-spiro[4.5]decan-4-ol.

EXAMPLE 10

(RS)-8-Cyclononyl-1-phenyl-1,8-diaza-spiro[4.5]decan-4-ol hydrochloride (1:2)

The title compound, white solid, m.p. 170° C. (dec.) and MS: m/e=357.3 (M+H$^+$) was prepared in accordance with the general method of example 1 from cyclononanone and (RS)-1-phenyl-1,8-diaza-spiro[4.5]decan-4-ol.

EXAMPLE 11

(RS)-8-Cyclodecyl-1-phenyl-1,8-diaza-spiro[4.5]decan-4-ol hydrochloride (1:2)

The title compound, white solid, m.p. 170° C. (dec.) and MS: m/e=371.3 (M+H$^+$) was prepared in accordance with the general method of example 1 from cyclodecanone and (RS)-1-phenyl-1,8-diaza-spiro[4.5]decan-4-ol.

EXAMPLE 12

8-(Decahydro-azulen-2-yl)-1-phenyl-1,8-diaza-spiro[4.5]decan-4-ol hydrochloride (1:1) (mixture of diastereoisomers)

The title compound, white solid, m.p. 265° C. (dec.) and MS: m/e=369.4 (M+H$^+$) was prepared in accordance with the general method of example 1 from (3aRS, 8aRS)-decahydro-azulen-2-on and (RS)-1-phenyl-1,8-diaza-spiro[4.5]decan-4-ol.

EXAMPLE 13

8-(Octahydro-inden-2-yl)-1-phenyl-1,8-diaza-spiro[4.5]decan-4-ol hydrochloride (1:2) (mixture of diastereoisomers)

The title compound, white solid, m.p. 236° C. (dec.) and MS: m/e=354 (M$^+$) was prepared in accordance with the general method of example 1 from cis-octahydro-inden-2-one and (RS)-1-phenyl-1,8-diaza-spiro[4.5]decan-4-ol.

EXAMPLE 14

(RS)-8-Cyclooctyl-1-phenyl-1,8-diaza-spiro[4.5]decan-4-ol hydrochloride (1:2)

The title compound, white solid, m.p. 173° C. (dec.) and MS: m/e=342 (M$^+$) was prepared in accordance with the general method of example 1 from cyclooctanone and (RS)-1-phenyl-1,8-diaza-spiro[4.5]decan-4-ol.

EXAMPLE 15

8-(Bicyclo[6.2.0]dec-9-yl)-1-phenyl-1,8-diaza-spiro [4.5]decan-4-ol hydrochloride (1:2) (mixture of diastereoisomers)

To a stirred solution of cis-bicyclo[6.2.0]dec-9-one (0.79 g, 5.2 mmol) in THF (10 ml) were added at RT tetraisopropyl-orthotitanate (1.9 ml, 6.5 mmol) and (RS)-1-phenyl-1,8-diaza-spiro[4.5]decan-4-ol (1.2 g, 5.2 mmol). The mixture was stirred at RT for 20 h and evaporated. The residue was dissolved in THF (4 ml)-ethanol (14 ml), sodium cyanoborohydride (0.25 g, 4.0 mmol) was added and the mixture was stirred at RT for 20 h. Water was added, the suspension was filtered and the filtrate was evaporated. Column chromatography on silica gel (dichloromethane-methanol-ammonia 26:1.0.1) and crystallization from 3N MeOH—HCl/diethyl ether yielded the title compound (0.86 g, 38%) as a white solid, m.p. 174° C. (dec.) and MS: m/e=369.4 (M+H$^+$).

EXAMPLE 16

8-(Acenaphthen-1-yl)-1-phenyl-1,8-diaza-spiro[4.5] decan-4-ol hydrochloride (1:2) (mixture of diastereoisomers)

To a stirred solution of (RS)-8-(acenaphthen-1-yl)-1-phenyl-1,8-diaza-spiro[4.5]decane-2,4-dione (0.67 g, 1.7 mmol) in THF (35 ml) was added at RT lithium aluminiumhydride (128 mg, 3.4 mmol) and the reaction mixture was boiled under reflux for 7 h. Water (20 drops) was added slowly at RT to the stirred solution and afterwards the reaction mixture was dried (Na$_2$SO$_4$) and filtered. The filtrate was evaporated and the crude product purified by column chromatography on silica gel (ethyl acetate/hexane 9:1) to yield (RS)-8-acenaphten-1-yl-1-phenyl-1,8-diaza-spiro[4.5]decane (50 mg/see example 20) as a pale yellow oil and 8-(acenaphthen-1-yl)-1-phenyl-1,8-diaza-spiro[4.5] decan-4-ol (127 mg) as a pale brown foam, which while stirring was dissolved in 3N MeOH—HCl (0.5 ml) and treated with diethyl ether (15 ml). After 1 h the solid was filtered off to yield the desired product (128 mg, 55%) as a pale brown solid, m.p. 196° and MS: m/e=385.3 (M+H$^+$).

Better yields are observed by first reducing (RS)-8-acenaphten-1-yl)-1-phenyl-1,8-diaza-spiro[4.5]decane-2,4-dione with sodium borohydride (see example 21) and afterwards with lithium aluminiumhydride as described in this example.

EXAMPLE 17

8-(2,3-Dihydro-1H-phenalen-1-yl)-1-phenyl-1,8-diaza-spiro[4.5]decan-4-ol hydrochloride (1:2) (mixture of diastereoisomers)

The title compound, pale brown solid, m.p. 197° C. (dec.) and MS: m/e=399.4 (M+H$^+$) was prepared in accordance with the general method of examples ag and 16 from (RS)-N-[4-Cyano-1-(2,3-dihydro-1H-phenalen-1-yl)-piperidin-4-yl]-N-phenyl-acetamide.

EXAMPLE 18

8-(2,3,3a,4,5,6-Hexahydro-1H-phenalen-1-yl)-1-phenyl-1,8-diaza-spiro[4.5]decan-4-ol hydrochloride (1:2) (mixture of diastereoisomers)

The title compound, white solid, m.p. 195° C. and MS: m/e=403.4 (M+H$^+$) was prepared in accordance with the general method of example 16 from (1RS,3aRS)-8-(2,3,3a, 4,5,6-hexahydro-1H-phenalen-1-yl)-1-phenyl-1,8-diaza-spiro[4.5]decane-2,4-dione.

EXAMPLE 19

(RS)-8-Acenaphthen-1-yl-1-phenyl-1,8-diaza-spiro [4.5]decane hydrochloride (1:1)

A stirred solution of (RS)-8-acenaphthen-1-yl-1-phenyl-1,8-diaza-spiro[4.5]decane (50 mg/see example 16) in 3N MeOH—HCl (0.2 ml) was treated with diethyl ether (5 ml). After 1 h the solid was filtered off to yield the desired product (50 mg, 91%) as a pale brown solid, m.p. 195° C and MS: m/e=369.4 (M+H$^+$).

EXAMPLE 20

(RS)-8-Acenaphthen-1-yl-1-phenyl-1,8-diaza-spiro [4.5]decan-4-one hydrochloride (1:1.4)

A mixture of 8-(acenaphthen-1-yl)-1-phenyl-1,8-diaza-spiro[4.5]decan-4-ol (0.25 g, 0.65 mmol; as a mixture of diastereoisomers), 4-methylmorpholine-4-oxide (176 mg, 1.3 mmol), tetra-n-propylammonium-perruthenate (22.8 g, 0.065 mmol) and powdered sieves (4A, 0.5 g) in dichloromethane (10 ml) was stirred at RT for 1 h. The reaction mixture was filtered, evaporated and purified by column chromatography on silica gel (ethyl acetate) to give an oil (150 mg) which while stirring was dissolved in 3N MeOH—HCl (1 ml) and treated with diethyl ether (50 ml). After 2 h the solid was filtered off to yield the desired product (150 mg, 53%) as a pale brown solid, m.p. 174° C. and MS: m/e=383.3 (M+H$^+$).

EXAMPLE 21

(RS)-8-(Acenaphthen-1-yl)-4-hydroxy-1-phenyl-1,8-diaza-spiro[4.5]decan-2-one hydrochloride (1:1) (mixture of diastereoisomers)

To a stirred solution of (RS)-8-(acenaphthen-1-yl)-1-phenyl-1,8-diaza-spiro[4.5]decane-2,4-dione (0.17 g, 0.43 mmol) in MeOH (5 ml) was added at RT sodium borohydride (19 mg, 0.5 mmol) and stirring was continued for 1.5 h. The reaction mixture was poured in brine (20 ml) and extracted with dichloromethane (2×40 ml. The combined organic layers were dried (MgSO$_4$) and evaporated. The crude product was purified by column chromatography on silica gel (dichloromethane/methanol 97.3) to give 170 mg of a pale yellow foam which while stirring was dissolved in 3N MeOH-HCl (0.5 ml) and treated with diethyl ether (15 ml). After 3 h the solid was filtered off to yield the desired product (103 mg, 55%) as a pale brown solid, m.p. 221° C. and MS: m/e=399.4 (M+H$^+$).

EXAMPLE 22

8-Bicyclo[6.2.0]dec-9-yl-1-phenyl-1,8-diaza-spiro [4.5]decan-4-one hydrochloride (1:1) (mixture of diastereoisomers)

The title compound, pale brown solid, m.p. 140° C. (dec.) and MS: m/e=367.2 (M+H$^+$) was prepared in accordance with the general method of example 20 from 8-(bicyclo [6.2.0]dec-9-yl)-1-phenyl-1,8-diaza-spiro[4.5]decan-4-ol hydrochloride (mixture of diastereoisomers).

EXAMPLE 23

8-(Decahydro-azulen-2-yl)-1-phenyl-1,8-diaza-spiro [4.5]decan-4-ol (mixture of diastereoisomers)

Oxidation of 8-(decahydro-azulen-2-yl)-1-phenyl-1,8-diaza-spiro[4.5]decan-4-ol (mixture of diastereoisomers)

according to the general method of example 20 and formation of the fumarate with fumaric acid in diethyl ether yielded the title compound, pale brown solid, m.p. 219° C. and MS: m/e=367.3 (M+H$^+$).

EXAMPLE 24

8-Cyclooctyl-1-phenyl-1,8-diaza-spiro[4.5]decan-4-one fumarate (1:1)

Oxidation of (RS)-8-cyclooctyl-1-phenyl-1,8-diaza-spiro[4.5]decan-4-ol according to the general method of example 20 and formation of the fumarate with fumaric acid in diethyl ether yielded the title compound, pale brown solid, m.p. 197° C. and MS: m/e=341.3 (M+H$^+$).

EXAMPLE 25

(3aRS,7aSR)-8-(Octahydro-inden-2-yl)-1-phenyl-1, 8-diaza-spiro[4.5]decan-4-one fumarate (1:1)

Oxidation of 8-(octahydro-inden-2-yl)-1-phenyl-1,8-diaza-spiro[4.5]decan-4-ol (mixture of diastereoisomers) according to the general method of example 20 and formation of the fumarate with fumaric acid in diethyl ether yielded the title compound, pale brown solid, m.p. 225° C. and MS: m/e=353.4 (M+H$^+$).

EXAMPLE 26

(1RS,3aRS)-8-(2,3,3a,4,5,6-Hexahydro-1H-phenalen-1-yl)-1-phenyl-1,8-diaza-spiro[4.5]decan-4-one fumarate (1:1)

Oxidation of 8-(2,3,3a,4,5,6-hexahydro-1H-phenalen-1-yl)-1-phenyl-1,8-diaza-spiro[4.5]decan-4-ol (mixture of diastereoisomers) according to the general method of example 20 and formation of the fumarate with fumaric acid in diethyl ether yielded the title compound, pale brown solid, m.p. 144° C. and MS: m/e=401.5 (M+H$^+$).

EXAMPLE 27

8-Cyclodecyl-1-phenyl-1,8-diaza-spiro[4.5]decan-4-one fumarate (1:1)

Oxidation of (RS)-8-cyclodecyl-1-phenyl-1,8-diaza-spiro[4.5]decan-4-ol according to the general method of example 20 and formation of the fumarate with fumaric acid in diethyl ether yielded the title compound, pale brown solid, m.p. 177° C. and MS: m/e=369.4 (M+H$^+$).

EXAMPLE 28

8-Cyclononyl-1-phenyl-1,8-diaza-spiro[4.5]decan-4-one fumarate (1:1)

Oxidation of (RS)-8-cyclononyl-1-phenyl-1,8-diaza-spiro[4.5]decan-4-ol according to the general method of example 20 and formation of the fumarate with fumaric acid in diethyl ether yielded the title compound, pale brown solid, m.p. 185° C. and MS: m/e=355.3 (M+H$^+$).

EXAMPLE 29

(3aRS,7aSR)-8-(Octahydro-inden-2-yl)-1-phenyl-1, 8-diaza-spiro[4.5]decane fumarate (1:0.5)

The title compound, pale yellow solid, m.p. 264° C. and MS: m/e=339.4 (M+H$^+$) was prepared in accordance with the general method of example 1 from cis-octahydro-inden-2-one and 1-phenyl-1,8-diaza-spiro[4.5]decane.

EXAMPLE 30

8-Cyclodecyl-1-phenyl-1,8-diaza-spiro[4.5]decane fumarate (1:0.5)

The title compound, white solid, m.p. 167° C. and MS: m/e=355.54 (M+H$^+$) was prepared in accordance with the general method of example 1 from cyclodecanone and 1-phenyl-1,8-diaza-spiro[4.5]decane.

EXAMPLE 31

(RS)-8-(cis-4-Isopropyl-cyclohexyl)-4-methoxy-1-phenyl-1,8-diaza-spiro[4.5]decane hydrochloride (1:1)

RS)-8-(cis-4-Isopropyl-cyclohexyl)-1-phenyl-1,8-diaza-spiro[4.5]decan-4-ol hydrochloride (0.3 mmol) was dissolved in dimethylformamide (15 ml), sodium hydride (1.2 mmol) was added and the mixture stirred for 1 h at room temperature. Dimethylsulfate (0.9 mmol) was added and stirring continued for 5 h. The mixture was quenched with ice-water (10 ml) and saturated sodiumbicarbonate solution (10 ml) and extracted three times with dichloromethane. The organic phases were pooled, dried with Na$_2$SO$_4$ and concentrated. Chromatography on silica gel (ethyl acetate) yielded the desired product which was crystallized as its HCl-salt from ethanol. 55 mg (44%) (RS)-8-(cis-4-isopropyl-cyclohexyl)-4-methoxy-1-phenyl-1,8-diaza-spiro[4.5]decane hydrochloride (1:1) as a colorless solid, m.p. 214–215° C. and MS: m/e=371.4 (M+H$^+$).

EXAMPLE 32

8-(trans-4-Isopropyl-cyclohexyl)-1-phenyl-1,8-diaza-spiro[4.5]decan-4-one hydrochloride (1:1)

The title compound, m.p. 237–238° C. and MS: m/e=355.4 (M+H$^+$) was prepared in accordance with the general method of example 5 from (RS)-8-(trans-4-isopropyl-cyclohexyl)-1-phenyl-1,8-diaza-spiro[4.5]decan-4-ol.

EXAMPLE 33

(R)-8-(cis-4-Isopropyl-cyclohexyl)-1-phenyl-1,8-diaza-spiro[4.5]decan-4-ol hydrochloride (1:1)

(1S,2R)-1-Amino-2-indanol (0.05 mmol) was dissolved in tetrahydrofurane (2 ml), borane-dimethylsulfide (0.34 mmol) was added and the mixture was stirred for 16 h at room temperature. A solution of 8-(cis-4-isopropyl-cyclohexyl)-1-phenyl-1,8-diaza-spiro[4.5]decan-4-one (0.5 mmol) dissolved in tetrahydrofurane (4 ml) was then added slowly to this mixture. The reaction was quenched with methanol (1 ml) and water (20 ml) and extracted three times with methylene chloride. The organic phases were pooled, dried with Na$_2$SO$_4$ and concentrated. Chromatography on silica gel (ethyl acetate) yielded the desired product which was crystallized as its HCl-salt from ethyl acetate. 20 mg (10%) (R)-8-(cis-4-isopropyl-cyclohexyl)-1-phenyl-1,8-diaza-spiro[4.5]decan-4-ol hydrochloride (1:1)as a colorless solid, m.p.>250° C. and MS: m/e=357.3 (M+H$^+$).

EXAMPLE 34

(S)-8-(cis-4-Isopropyl-cyclohexyl)-1-phenyl-1,8-diaza-spiro[4.5]decan-4-ol hydrochloride (1:1)

The title compound, m.p.>250° C. and MS: m/e=357.3 (M+H$^+$) was prepared in accordance with the general method of example 33 from 8-(cis-4-isopropyl-cyclohexyl)-1-phenyl-1,8-diaza-spiro[4.5]decan-4-one and (1R,2S)-1-amino-2-indanol.

EXAMPLE 35

(RS)-8-(4-Methyl-indan-2-yl)-1-phenyl-1,8-diaza-spiro[4.5]decan-4-one hydrochloride (1:1)

The title compound, m.p.>250° C. and MS: m/e=361.3 (M+H$^+$) was prepared in accordance with the general method of example 5 from the mixture of (RS)- and (SR)-8[(RS)-(4-Methyl-indan-2-yl)]-1-phenyl-1,8-diaza-spiro[4.5]decan-4-ol.

EXAMPLE 36

8-(Octahydro-inden-2-yl)-4-methoxy-1-phenyl-1,8-diaza-spiro[4.5]decane hydrochloride (1:2) (mixture of diastereoisomers)

The product of example 13 (130 mg) was dissolved in 10 ml dry DMF and 75 mg of sodium hydride (50% in mineral oil) was added at room temperature. The reaction mixture was stirred for one hour after which 100 ml of dimethylsulfate were added. Stirring was continued for 24 h, then the reaction mixture was quenched by the addition of ice cold 1N hydrochloric acid. The aqueous layer was extracted two times with ether and the extracts were discarded. The aqueous layer was then basified with 2N sodium hydroxide solution and extracted three times with ethyl acetate. The combined organic extracts were washed with water and brine, concentrated and subjected to preparative thin layer-chromatography to yield the free base (60 mg) as a clear oil that crystallized on standing. Formation of the hydrochloride under standard conditions furnished the title compound, m/z=369 [M+H].

EXAMPLE 37

8-(Octahydro-inden-2-yl)-1-cyclohexyl-1,8-diaza-spiro[4.5]decan-4-ol hydrochloride (1:2) (mixture of diastereoisomers)

The product of example 13 (50 mg) was dissolved in 150 ml methanol and 50 mg of platinium oxide were added. The mixture was hydrogenated for 38 h under 20 atmospheres hydrogen gas at room temperature. Then the reaction mixture was filtered and the solvent evaporated. The residue purified by preparative thin layer chromatography to yield the free base as a slightly yellow solid (15 mg). Formation of the hydrochloride under standard conditions furnished the title compound, m/z=361 [M+H].

EXAMPLE 38

(RS)-8-(cis-4-Isopropyl-cyclohexyl)-4-phenyl-1-thia-4,8-diaza-spiro[4.5]decane fumarate (1:2)

cis-(4-isopropyl-cyclohexyl)-piperidine-4-one (224 mg) was dissolved in 15 ml dichloromethane and 139 ml of N-phenyl-2-amino ethanethiol were added under argon. The reaction mixture was cooled to 0° C. and 630 ml borontriflouride-diethyl ether-complex (freshly distilled) was added. After 1 hour, the reaction was quenched with one ml of aqueous ammonium hydrochloride solution. The aqueous layer was extracted two times with dichloromethane and ether and the extracts dried over sodium sulfate. Evaporation of the solvent gave a yellow oil, which was purified by preparative thin layer chromatography to yield the title compound (72 mg) which was converted to the fumarate salt using standard conditions. m.p. 175–176° C.; m/z=359 [M+H]$^+$.

EXAMPLE 39

8-(cis-4-Isopropyl-cyclohexyl)-1-phenyl-1,8-diaza-spiro[4,5]dec-3-ene-3,4-dicarboxylic acid dimethylester hydrochloride (1:1.33)

[1-(cis-4-Isopropyl-cyclohexyl)-piperidin-4-ylidene] phenyl-amine (1.00 g, 3.35 mmol) was treated at 0° C. with (trimethylsilyl)methyl trifluoromethane sulfonate (792 mg, 3.35 mmol). 1,2-Dimethoxy ethane (35 ml) and dimethyl acetylenedicarboxylate (2.38 g, 16.8 mmol) followed by caesium fluoride (509 mg, 3.35 mmol) were added and the reaction mixture was stirred at room temperature for 40 h. The solvent was evaporated, the residue taken up in ethyl acetate and extracted with water. The organic phase was dried with MgSO$_4$ and concentrated. Chromatography on silica gel (hexane/ethyl acetate 8:1) followed by thin layer chromatography (toluene/ethyl acetate 10:1) gave the desired product which was precipitated as its HCl-salt from ether. 46 mg (2.7%) (8-(cis-4-isopropyl-cyclohexyl)-1-phenyl-1,8-diaza-spiro[4,5]dec-3-ene-3,4-dicarboxylic acid dimethylester hydrochloride (1:1.33) as a white solid, dec.>200° C., MS: m/e=455.5 (M+H$^+$).

EXAMPLE 40

Mixture of (RS)- and (SR)-(2RS,4aSR,8aRS)-8-Decahydro-naphthalen-2-yl)-4-hydroxy-1-phenyl-1,8-diaza-spiro[4.5]decan-2-one hydrochloride (1:1)

The title compound, m.p.>166° C. dec. and MS: m/e=383.3 (M+H$^+$) was prepared in accordance with the general method of example 21 from (2RS,4aSR,8aRS)-8-(decahydronaphthalen-2-yl)-4-hydroxy-1-phenyl-1,8-diaza-spiro[4.5]decan-2,4-dione.

EXAMPLE 41

Mixture of (RS)- and (SR)-8-[(2RS,4aSR,8aRS)-decahydro-naphthalen-2-yl]-1-phenyl-1,8-diaza-spiro[4.5]decan-4-ol hydrochloride (1:1)

The title compound, m.p.>250° C. dec. and MS: m/e=369.4 (M+H$^+$) was prepared in accordance with the general method of example 16 from (RS)- and (SR)-(2RS,4aSR,8aRS)-8-(decahydro-naphthalen-2-yl)-4-hydroxy-1-phenyl-1,8-diaza-spiro[4.5]decan-2-one.

EXAMPLE 42

(2RS,4aSR,8aRS)-8-(Decahydro-naphthalen-2-yl)-1-phenyl-1,8-diaza-spiro[4.5]decan-4-one hydrochloride (1:1)

The title compound, m.p. 250–251° C. dec. and MS: m/e=367.3 (M+H$^+$) was prepared in accordance with the general method of example 5 from (RS)- and (SR)-8-[(2RS,4aSR,8aRS)-decahydro-naphthalen-2-yl]-1-phenyl-1,8-diaza-spiro[4.5]decan-4-ol.

EXAMPLE 43

Mixture of (RS)- and (SR)-8-[(1RS,3aSR)-2,3,3a,4,5,6-hexahydro-1H-phenalen-1-yl]-1-phenyl-1,8-diaza-spiro[4.5]decan-4-ol fumarate (1:1)

The title compound, light brown solid, m.p. 205° C. and MS: m/e=403.5 (M+H$^+$) was prepared in accordance with the general method of example 17 from (1RS,3aSR)-8-(2,3,3a,4,5,6-hexahydro-1H-phenalen-1-yl)-1-phenyl-1,8-diaza-spiro[4.5]decane-2,4-dione and subsequent formation of the fumarate.

(1RS,3aSR)-8-(2,3,3a,4,5,6-Hexahydro-1H-phenalen-1-yl)-1-phenyl-1,8-diaza-spiro[4.5]decane-2,4-dione was prepared from (1RS,3aSR)-1-(2,3,3a,4,5,6-hexahydro-1H-phenalen-1-yl)-piperidin-4-one as described for (1RS,3aRS)-8-(2,3,3a,4,5,6-hexahydro-1H-phenalen-1-yl)-1-phenyl-1,8-diaza-spiro[4.5]decane-2,4-dione.

EXAMPLE 44

Mixture of (RS)- and (SR)-8-[(1RS,3aRS)-2,3,3a,4,5,6-hexahydro-1H-phenalen-1-yl)-4-methoxy-1-phenyl-1,8-diaza-spiro[4.5]decane fumarate (1:1)

Methylation of a mixture of (RS)- and (SR)-8-(1RS,3aRS)-2,3,3a,4,5,6-hexahydro-1H-phenalen-1-yl)-1-phenyl-1,8-diaza-spiro[4.5]decan-4-ol according to the general method of example 31 and formation of the fumarate with fumaric acid in diethyl ether yielded the title compound, pale brown solid, m.p. 206° C. and MS: m/e=417.3 (M+H$^+$).

EXAMPLE 45

Mixture of (RS)- and (SR)-8-[(RS)-acenaphthen-1-yl]-4-methoxy-1-phenyl-1,8-diaza-spiro[4.5]decane fumarate (1:1)

Methylation of a mixture of (RS)- and (SR)-8-(acenaphthen-1-yl)-1-phenyl-1,8-diaza-spiro[4.5]decan-4-ol according to the general method of example 31 and formation of the fumarate with fumaric acid in diethyl ether yielded the title compound, pale brown solid, m.p. 208° C. and MS: m/e=399.4 (M+H$^+$).

EXAMPLE 46

(RS)-8-Cyclodecyl-4-methoxy-1-phenyl-1,8-diaza-spiro[4.5]decane hydrochloride (1:2)

Methylation of (RS)-8-cyclodecyl-1-phenyl-1,8-diaza-spiro[4.5]decan-4-ol according to the general method of example 31 and formation of the fumarate with fumaric acid in diethyl ether yielded the title compound, white solid, m.p. 170° C. (dec.) and MS: m/e=385.4 (M+H$^+$).

EXAMPLE 47

(RS)-8-Cyclooctyl-4-methoxy-1-phenyl-1,8-diaza-spiro[4.5]decane hydrochloride (1:1.5)

Methylation of (RS)-8-cyclooctyl-1-phenyl-1,8-diaza-spiro[4.5]decan-4-ol according to the general method of example 31 and formation of the fumarate with fumaric acid in diethyl ether yielded the title compound, white solid, m.p. 160° C. (dec.) and MS: m/e=357.3 (M+H$^+$).

EXAMPLE 48

8-Bicyclo[6.2.0]dec-9-yl-4-methoxy-1-phenyl-1,8-diaza-spiro[4.5]decane hydrochloride (1:1) (mixture of distereoisomers; config. in bicyclodecane moiety at C1 and C8 cis)

Methylation of 8-(bicyclo[6.2.0]dec-9-yl)-1-phenyl-1,8-diaza-spiro[4.5]decan-4-ol (mixture of distereoisomers; config. in bicyclodecane moiety at C1 and C8 cis) according to the general method of example 31 and formation of the fumarate with fumaric acid in diethyl ether yielded the title compound, white solid, m.p. 170° C. (dec.) and MS: m/e=383.3 (M+H$^+$).

EXAMPLE 49

(RS)-8-Cyclononyl-4-methoxy-1-phenyl-1,8-diaza-spiro[4.5]decane fumarate (1:1)

Methylation of (RS)-8-cyclononyl-1-phenyl-1,8-diaza-spiro[4.5]decan-4-ol according to the general method of example 31 and formation of the fumarate with fumaric acid in diethyl ether yielded the title compound, pale brown solid, m.p. 196° C. (dec.) and MS: m/e=371.3 (M+H$^+$).

EXAMPLE 50

8-(Decahydro-azulen-2-yl)-4-methoxy-1-phenyl-1,8-diaza-spiro[4.5]decane fumarate (1:1) (mixture of the diastereoisomers)

Methylation of 8-(decahydro-azulen-2-yl)-1-phenyl-1,8-diaza-spiro[4.5]decan-4-ol (mixture of diastereoisomers) according to the general method of example 31 and formation of the fumarate with fumaric acid in diethyl ether yielded the title compound, white solid, m.p. 260° C. (dec.) and MS: m/e=383.3 (M+H$^+$).

EXAMPLE 51

(3RS, 4SR)-8-(cis-4-Isopropyl-cyclohexyl)-1-phenyl-1,8-diaza-spiro[4,5]decane-3,4-dicarboxylic acid dimethylester hydrochloride (1:1)

The title compound, MS: m/e=457.5 (M+H$^+$) was prepared in accordance with the general method of example 39 from [1-(cis-4-isopropyl-cyclohexyl)-piperidin-4-ylidene]phenyl-amine and dimethyl maleate.

EXAMPLE 52

(3RS, 4RS)-8-(cis-4-Isopropyl-cyclohexyl)-1-phenyl-1,8-diaza-spiro[4,5]decane-3,4-dicarboxylic acid dimethylester hydrochloride (1:1)

The title compound, dec.>200° C. and MS: m/e=457.5 (M+H$^+$) was prepared in accordance with the general method of example 39 from [1-(cis-4-isopropyl-cyclohexyl)-piperidin-4-ylidene]phenyl-amine and dimethyl fumarate.

EXAMPLE 53

8-(cis-4-Isopropyl-cyclohexyl)-3,4-diphenyl-1-oxa-2,4,8-triaza-spiro[4,5]dec-2-ene hydrochloride (1:1)

[1-(cis-4-Isopropyl-cyclohexyl)-piperidin-4-ylidene]phenyl-amine (1.20 g, 4.00 mmol), benzohydroximioyl chloride (2.25 g, 8.00 mmol) and triethyl amine (810 mg, 8.00 mmol) were stirred at room temperature in 70 ml tetrahydrofuran for 24 h. The solvent was evaporated, the residue taken up in methylene chloride and extracted with water. The organic phase was dried with MgSO$_4$ and concentrated. Chromatography on silica gel (hexane/ethyl acetate 9:1) followed by recrystallization from diisopropyl ether gave 40 mg (2.4%) of the desired product as colourless crystalls, m.p.=131° C. and MS: m/e=418.4 (M+H$^+$). It was precipitated as its HCl-salt from ether/dioxane.

SYNTHESES OF INTERMEDIATES

Example aa (RS)-1-Phenyl-1,8-diaza-spiro[4.5]decan-4-ol (RS)-8-Benzyl-1-phenyl-1,8-diaza-spiro[4.5]decan-4-ol (7.8 mmol) was dissolved in methanol (100 ml) and ethylacetate (100 ml). Palladium on carbon (10%, 0.2 g) was added and the mixture was hydrogenated at room temperature and normal pressure. Filtration and evaporation yielded the desired product. 1.8 g (99%) (RS)-1-phenyl-1,8-diaza-spiro[4.5]decan-4-ol as a beige solid, m.p. 141–144° C. and MS: m/e=232 (M⁺).

Example ab (RS)-N-(1-Acenaphthen-1-yl)-4-cyano-piperidin-4-yl)-N-phenyl-acetamide To a stirred mixture of pyridine (4.5 ml, 55.5 mmol), acetyl chloride (2 ml, 27.7 mmol) and DMAP (20 mg) in dichloromethane (150 ml) was added dropwise at RT a solution of (RS)-4-phenylamino-1-(acenaphthen-1-yl)-piperidine-4-carbonitrile (4.9 g, 13.9 mmol) in dichloromethane (100 ml). After 21 h the reaction mixture was poured in sat. NaHCO$_3$ (100 ml) and the layers were separated. The aqueous phase was extracted with dichloromethane (150 ml), the combined organic layers were washed with sat. NaHCO$_3$ (100 ml), brine (100 ml), dried (MgSO$_4$) and evaporated. The crude product was purified by column chromatography on silica gel (ethyl acetate/hexane 4:1) to give beside 1.49 g (RS)-4-phenylamino-1-(acenaphthen-1-yl)-piperidine-4-carbonitrile (1.49, 30%) the desired product (2.9 g, 53%) as a pale brown foam, MS: m/e=396.2 (M+H⁺).

Example ac (RS)-N-[4-Cyano-1-(2,3-dihydro-1H-phenalen-1-yl)-piperidin-4-yl]-N-phenyl-acetamide The title compound, pale brown foam, MS: m/e=410.4 (M+H⁺) was prepared in accordance with the general method of example ab from (RS)-4-phenylamino-1-(2,3-dihydro-1H-phenalen-1-yl)-piperidine-4-carbonitrile.

Example ad (1RS,3aRS)-1-(2,3,3a,4,5,6-Hexahydro-1H-phenalen-1-yl)-piperidin-4-one and (1RS,3aSR)-1-(2,3,3a,4,5,6-Hexahydro-1H-phenalen-1-yl)-piperidin-4-one To a stirred mixture of (RS)-2,3,3a,4,5,6-hexahydro-phenalen-1-one (3.53 g, 19.0 mmol), hydroxylamine hydrochloride (2.2 g, 32.0 mmol) and water (14 ml) was added dropwise at 75° C. MeOH (18 ml) and afterwards a solution of sodium acetate (6.7 g, 49.9 mmol) in water (13 ml). Stirring was continued over a period of 1.5 h, water (40 ml) was added and after cooling (ice bath) the solid was collected by filtration. After drying in vacuo the crude product was dissolved in 3.5 N NH$_3$/MeOH (160 ml) and hydrogenated over Raney-Nickel (2.9 g, washed with MeOH) at RT for 65 h. The catalyst was filtered off, the solution evaporated in vacuo to give a green oil (3.52 g), which was dissolved in ethanol (36.5 ml). Potassium carbonate (0.26 g, 1.9 mmol) and 1-ethyl-1-methyl-4-oxo-piperidinium iodide (7.0 g, 26.2 mmol) dissolved in water (13 ml) were added and the mixture was refluxed for 45 min. The reaction mixture was poured into 3N sodium hydroxide solution (160 ml) and extracted with ethylacetate (2×300 ml). The combined organic layers were dried (MgSO$_4$) and evaporated. Intensive column chromatography on silica gel (toluene/ethylacetate 9:1) yielded (1RS,3aSR)-1-(2,3,3a,4,5,6-hexahydro-1H-phenalen-1-yl)-piperidin-4-one (2.37 g, 47%) and (1RS,3aRS)-1-(2,3,3a,4,5,6-hexahydro-1H-phenalen-1-yl)-piperidin-4-one (1.97 g, 39%). Both compounds are pale yellow oils, MS: m/e=269 (M⁺).

Example ae (1RS,3aRS)-1-(2,3,3a,4,5,6-Hexahydro-1H-phenalen-1-yl)-4-phenylamino-piperidine-4-carbonitrile (1RS,3aRS)-1-(2,3,3a,4,5,6-Hexahydro-1H-phenalen-1-yl)-piperidin-4-one (2.62 g, 9.7 mmol) was dissolved in acetic acid (12 ml). Aniline (0.97 ml, 10.6 mmol) and trimethylsilylcyanide (1.2 ml, 9.7 mmol) were added and the mixture was stirred for 3 h at RT. The reaction mixture was poured into cold ammonia solution (40 ml), extracted with methylene chloride (2×200 ml) and brine (150 ml). The combined organic layers were combined, dried with magnesium sulfate and concentrated. Crystallization from diethylether/hexane yielded (1RS,3aRS)-1-(2,3,3a,4,5,6-Hexahydro-1H-phenalen-1-yl)-4-phenylamino-piperidine-4-carbonitrile (3.1 g, 86%) as a pale yellow solid, m.p. 142° C. and MS: m/e=372.4 (M+H⁺).

Example af (1RS,3aRS)-N-[4-Cyano-1-(2,3,3a,4,5,6-hexahydro-1H-phenalen-1-yl)-piperidin-4-yl]-N-phenyl-acetamide The title compound, pale brown foam, MS: m/e=410.4 (M+H⁺) was prepared in accordance with the general method of example ab from (1RS,3aRS)-1-(2,3,3a,4,5,6-Hexahydro-1H-phenalen-1-yl)-4-phenylamino-piperidine-4-carbonitrile.

Example ag (RS)-8-(Acenaphthen-1-yl)-1-phenyl-1,8-diaza-spiro[4.5]decane-2,4-dione To a stirred solution of (RS)-N-(1-acenaphthen-1-yl-4-cyano-piperidin-4-yl)-N-phenyl-acetamide (1.47 g, 3.7 mmol) in THF (75 ml) was added dropwise at −78° C. a freshly prepared solution of LDA (4.6 mmol) in THF (25 ml). Stirring was continued for 1 h at −78° C. and for additional 2 h at RT, the reaction mixture was poured in cooled brine (100 ml) and extracted with ethyl acetate (2×200 ml). The combined organic layers were washed with brine (100 ml), dried (MgSO$_4$) and evaporated to give a yellow foam (1.49 g). A stirred solution of the intermediate in MeOH (100 ml) and 1N HCl (30 ml) was boiled under reflux for 1 h and evaporated. To the residue was added 1 N NaOH (30 ml) and sat. NaHCO$_3$ (30 ml). The aqueous solution was extracted with dichloromethane (2×100 ml), washed with brine (70 ml), dried (MgSO$_4$) and evaporated. The crude product was purified by column chromatography on silica gel (dichloromethane/methanol 30:1) to yield the desired product (0.68 g, 46%) as a pale brown foam, MS: m/e=397.3 (M+H⁺).

Example ah (1RS,3aRS)-8-(2,3,3a,4,5,6-Hexahydro-1H-phenalen-1-yl)-1-phenyl-1,8-diaza-spiro[4.5]decane-2,4-dione The title compound, pale yellow foam, MS: m/e=415.4 (M+H⁺) was prepared in accordance with the general method of example ag from (1RS,3aRS)-N-[4-Cyano-1-(2,3,3a,4,5,6-hexahydro-1H-phenalen-1-yl)-piperidin-4-yl]-N-phenyl-acetamide.

Example ai

1-Phenyl-1,8-diaza-spiro[4.5]decane

The title compound, yellow oil, MS: m/e=217.3 (M+H⁺) was prepared in accordance with the general method of example aa from 8-benzyl-1-phenyl-1,8-diaza-spiro[4.5]decane.

Example aj cis-(4-(2-methyl-ethyl)-cyclohexyl)-piperidine-4-one cis-4-(2-methyl-ethyl)-cyclohexyl-amine hydrochloride (60.7 g) was dissolved in ethanol (725 ml). Potassium carbonate (51.8 g) and 1-ethyl-1-methyl-4-oxo-piperidinium iodide (126.6 g) dissolved in water (240 ml) were added and the mixture was refluxed for 1 hour. The reaction mixture was concentrated and extracted three times with dichloromethane. The combined organic layers were washed with aqueous bicarbonate and water, dried (MgSO$_4$) and evaporated. Filtration over silica gel (cyclohexane/ethylacetate 17:3) yielded 69.7 g of a yellow oil which was distilled to yield the title compound (75%) as a slightly yellow oil. b.p. 111° C./0.45 mbar; m/z=223 [M⁺·].

Example ak cis-[1-(4-Isopropyl-cyclohexyl)-piperidin-4-ylidene]phenyl-amine cis-1-(4-Isopropyl-cyclohexyl)-piperidine-4-one (5.0 g, 23.4 mmol), aniline (3.3 g, 35.3 mmol) and molecular sieves (20 g, 4A) were stirred in 100 ml pentane at room temperature for 6 days. The molecular sieves were filtered off and the solvent was evaporated. The crude product was used without any further purification.

Example al

(2RS,4aSR,8aRS)-8-(Decahydro-naphthalen-2-yl)-1-phenyl-1,8-diaza-spiro[4.5]decane-2,4-dione hydrochloride (1:1)

The title compound, m.p.>250° C. dec. and MS: m/e=381.3 (M+H⁺) was prepared in accordance with the general method described in Van Parys, Marc et al., Bull. Soc. Chim. Belg. (1981), 90(7), 749–55 from (2RS,4aSR,8aRS)-decahydro-naphthalen-2-ylamine.

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. Compounds of the general formula I

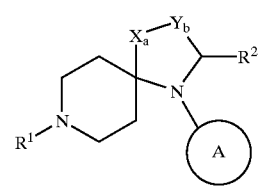

wherein

R$^1$ is C$_6$-cycloalkyl which is substituted by lower alkyl or —C(O)O-lower alkyl; C$_{7-10}$-cycloalkyl, which is substituted by lower alkyl or —C(O)O-lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; 2,3-dihydro-1H-phenalen-1-yl; 2,3,3a,4,5,6-hexahydro-1H-phenalen-1-yl or octahydro-inden-2-yl;

R$^2$ is hydrogen; lower alkyl; =O or phenyl, which is unsubstituted or substituted by lower alkyl, halogen or alkoxy;

is cyclohexyl or phenyl, which is unsubstituted or substituted by lower alkyl, halogen or alkoxy;

X is —CH(OH)—; —C(O)—; —CHR$^3$—; —CR$^3$=; —O—; —S—; —CH(COOR$^4$)— or —C(COOR$^4$)=;

Y is —CH$_2$—; —CH=; —CH(COOR$^4$)—, —C(COOR$^4$)=; or —C(CN)—;

R$^3$ is hydrogen or lower alkoxy;

R$^4$ is lower alkyl, cycloalkyl, phenyl, or benzyl and either a or b is optionally an additional bond, racemic mixtures and their corresponding enantiomers and pharmaceutically acceptable acid addition salts thereof.

2. A compound according to claim 1, wherein R$^1$ is C$_{6-10}$-cycloalkyl, optionally substituted by lower alkyl, R$^2$ is hydrogen, X is —CH(OH)—, —C(O)— or —CHOCH$_3$ and Y is —CH$_2$—.

3. A compound according to claim 2, (RS)-8-(cis-4-isopropyl-cyclohexyl)-1-phenyl-1,8-diaza-spiro[4.5]decan-4-ol.

4. A compound according to claim 2, (R)-8-(cis-4-isopropyl-cyclohexyl)-1-phenyl-1,8-diaza-spiro[4.5]decan-4-ol.

5. A compound according to claim 2, (S)-8-(cis-4-isopropyl-cyclohexyl)-1-phenyl-1,8-diaza-spiro[4.5]decan-4-ol.

6. A compound according to claim 2, 8-(cis-4-isopropyl-cyclohexyl)-1-phenyl-1,8-diaza-spiro[4.5]decan-4-one.

7. A compound according to claim 2, (RS)-8-(cis-4-isopropyl-cyclohexyl)-4-methoxy-1-phenyl-1,8-diaza-spiro[4.5]decane.

8. A compound according to claim 2, (RS)-8-cyclononyl-1-phenyl-1,8-diaza-spiro[4.5]decan-4-ol.

9. A compound according to claim 1, wherein R$^1$ is selected from the group consisting of decahydro-naphthalen-2-yl, 2,3,3a,4,5,6-hexahydro-1H-phenalen-1-yl, 4-methyl-indan-2-yl, octahydro-inden-2-yl and decahydro-azulen-2-yl; R$^2$ is hydrogen; X is —CH(OH)— or —CHOCH$_3$; and Y is —CH$_2$—.

10. A compound according to claim 9, (RS)- and (SR)-8-[(2RS,4aSR,8aRS)-decahydro-naphthalen-2-yl]-1-phenyl-1,8-diaza-spiro[4.5]decan-4-ol.

11. A compound according to claim 9, 8-(decahydro-naphthalen-2-yl)-1-phenyl-1,8-diaza-spiro[4.5]decan-4-ol.

12. A compound according to claim 9, 8-(2,3,3a,4,5,6-hexahydro-1H-phenalen-1-yl)-1-phenyl-1,8-diaza-spiro[4.5]decan-4-ol.

13. A compound according to claim 9, (RS)- and (SR)-8-[(RS)-(4-methyl-indan-2-yl)]-1-phenyl-1,8-diaza-spiro[4.5]decan-4-ol.

14. A compound according to claim 9, 8-(decahydro-azulen-2-yl)-1-phenyl-1,8-diaza-spiro[4.5]decan-4-ol.

15. A compound according to claim 9, 8-(octahydro-inden-2-yl)-4-methoxy-1-phenyl-1,8-diaza-spiro[4.5]decane (mixture of diastereoisomers).

16. A pharmaceutical composition comprising a therapeutically effective amount of a compound of formula I

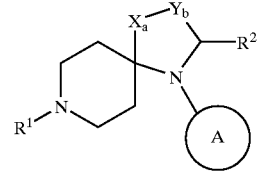

I wherein

R$^1$ is C$_6$-cycloalkyl which is substituted by lower alkyl or —C(O)O-lower alkyl; C$_{7-10}$-cycloalkyl, which is substituted by lower alkyl or —C(O)O-lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; 2,3-dihydro-1H-phenalen-1-yl; 2,3,3a,4,5,6-hexahydro-1H-phenalen-1-yl or octahydro-inden-2-yl;

R$^2$ is hydrogen; lower alkyl; =O or phenyl, which is unsubstituted or substituted by lower alkyl, halogen or alkoxy;

is cyclohexyl or phenyl, which is unsubstituted or substituted by lower alkyl, halogen or alkoxy;

X is —CH(OH)—; —C(O)—; —CHR$^3$—; —CR$^3$=; —O—; —S—; —CH(COOR$^4$)— or —C(COOR$^4$)=;

Y is —CH$_2$—; —CH=; —CH(COOR$^4$)—, —C(COOR$^4$)=; or —C(CN)—;

R$^3$ is hydrogen or lower alkoxy;

R$^4$ is lower alkyl, cycloalkyl, phenyl, or benzyl and either a or b is optionally an additional bond, as well as pharmaceutically acceptable salts thereof and a pharmaceutically acceptable carrier.

17. A method of treating disorders in mammals related to the orphanin FQ receptor selected from the group consisting of anxiety, stress, depression, trauma, Alzheimer's mediated memory loss, epilepsy, arterial blood pressure disorders, obesity, acute pain, chronic pain, Na+ excretion, control of water balance, and symptoms associated with drug withdrawal comprising administering to said mammal a therapeutically effective amount for treating said disorder of a compound of formula I

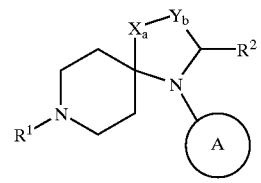

I wherein

R$^1$ is C$_{6-10}$-cycloalkyl, which is unsubstituted or substituted by lower alkyl or —C(O)O-lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; 2,3-dihydro- 1H-phenalen-1-yl; 2,3,3a,4,5,6-hexahydro-1H-phenalen-1-yl or octahydro-inden-2-yl;

$R^2$ is hydrogen; lower alkyl; =O or phenyl, which is unsubstituted or substituted by lower alkyl, halogen or alkoxy;

is cyclohexyl or phenyl, which is unsubstituted or substituted by lower alkyl, halogen or alkoxy;

X is —CH(OH)—; —C(O)—; —CHR$^3$—; —CR$^3$=; —O—; —S—; —CH(COOR$^4$)— or —C(COOR$^4$)=;

Y is —CH$_2$—; —CH=; —CH(COOR$^4$)—, —C(COOR$^4$)=; or —C(CN)—;

$R^3$ is hydrogen or lower alkoxy;

$R^4$ is lower alkyl, cycloalkyl, phenyl, or benzyl and either a or b is optionally an additional bond, as well as pharmaceutically acceptable salts thereof and a pharmaceutically acceptable carrier.

18. A process for preparing a compound of formula I as defined in claim 1, comprising reductively aminating a compound of formula

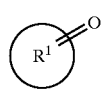

II with a compound of formula

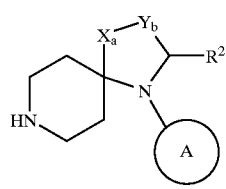

III wherein $R^1$ is $C_{6-10}$-cycloalkyl, which is unsubstituted or substituted by lower alkyl or —C(O)O-lower alkyl; decahydro-naphthalen-1-yl; decahydro-naphthalen-2-yl; indan-1-yl or indan-2-yl, which is unsubstituted or substituted by lower alkyl; decahydro-azulen-2-yl; bicyclo[6.2.0]dec-9-yl; acenaphthen-1-yl; 2,3-dihydro-1H-phenalen-1-yl; 2,3,3a,4,5,6-hexahydro-1H-phenalen-1-yl or octahydro-inden-2-yl;

$R^2$ is hydrogen; lower alkyl; =O or phenyl, which is unsubstituted or substituted by lower alkyl, halogen or alkoxy;

is cyclohexyl or phenyl, which is unsubstituted or substituted by lower alkyl, halogen or alkoxy;

X is —CH(OH)—; —C(O)—; —CHR$^3$—; —CR$^3$=; —O—; —S—; —CH(COOR$^4$)— or —C(COOR$^4$)=;

Y is —CH$_2$—; —CH=; —CH(COOR$^4$)—, —C(COOR$^4$)=; or —C(CN)—;

$R^3$ is hydrogen or lower alkoxy;

$R^4$ is lower alkyl, cycloalkyl, phenyl, or benzyl and either a or b may be an additional bond.

19. The process of claim 18 further comprising converting a racemic mixture of a compound of formula I into its enantomeric components thus obtaining substantially optically pure compounds.

20. The process of claim 18 further comprising converting a compound of formula I into a pharmaceutically acceptable salt thereof.

* * * * *

UNITED STATES PATENT AND TRADEMARK OFFICE
CERTIFICATE OF CORRECTION

PATENT NO. : 6,642,247 B2
DATED : November 4, 2003
INVENTOR(S) : Geo Adam et al.

It is certified that error appears in the above-identified patent and that said Letters Patent is hereby corrected as shown below:

<u>Title page,</u>
Item [73], Assignee, "Hoffman-La Roche Inc." shoud read -- Hoffmann-La Roche Inc. --.

Signed and Sealed this

Twentieth Day of April, 2004

JON W. DUDAS
*Acting Director of the United States Patent and Trademark Office*